United States Patent [19]

McGuire et al.

[11] Patent Number: 5,447,843

[45] Date of Patent: *Sep. 5, 1995

[54] HEAT SHOCK/STRESS RESPONSE PROTEINS AND PROGNOSIS IN CANCER

[75] Inventors: William L. McGuire, deceased, late of San Antonio, by John W. Robb, legal representative; Gary M. Clark, San Antonio; Gary C. Chamness, San Antonio; Atul K. Tandon, San Ramon; Suzanne A. Fuqua, San Antonio, all of Tex.

[73] Assignee: Board of Regents, The University of Texas System, Austin, Tex.

[*] Notice: The portion of the term of this patent subsequent to Feb. 23, 2010 has been disclaimed.

[21] Appl. No.: 949,630

[22] PCT Filed: Apr. 12, 1991

[86] PCT No.: PCT/US91/02536

§ 371 Date: Nov. 25, 1992

§ 102(e) Date: Nov. 25, 1992

[87] PCT Pub. No.: WO/9116632

PCT Pub. Date: Oct. 31, 1991

Related U.S. Application Data

[63] Continuation-in-part of Ser. No. 509,377, Apr. 12, 1990, Pat. No. 5,188,964.

[51] Int. Cl.$^6$ .................. G01N 33/574; G01N 33/53; C12Q 1/68
[52] U.S. Cl. ........................ 435/6; 435/7.23; 435/7.2; 435/7.9; 435/7.92; 435/975; 436/63; 436/64; 436/813; 436/516
[58] Field of Search ............. 435/7.23, 7.2, 7.9, 435/7.92, 975; 436/516, 63, 64, 813

[56] References Cited

U.S. PATENT DOCUMENTS 5,188,964 2/1993 McGuire et al. ............. 436/64

Primary Examiner—Toni R. Scheiner
Attorney, Agent, or Firm—Arnold, White & Durkee

[57] ABSTRACT

The invention relates to a method of predicting disease-free survival in cancer patients by relating the number and amount of stress response proteins in cancer tissue to the probability of tumor recurrence. Particular heat shock/stress response proteins useful in the determination of tumor recurrence are the stress response proteins, hsp70, hsp90, hsp27, and glucose regulated protein grp94. Specific levels of the stress response proteins relative to an internal standard are identified, above which the probability of tumor recurrence is highly significant. Kit methods are disclosed which could enable determination of the stress proteins by an antibody assay.

24 Claims, 6 Drawing Sheets

HEAT SHOCK/STRESS RESPONSE PROTEINS AND PROGNOSIS IN CANCER

The United States Government may have certain rights in the present invention pursuant to the terms of Grant No. CA 11378 awarded by the National Cancer Institute.

This is a continuation-in-part of U.S. patent application Ser. No. 07/509,377 filed Apr. 12, 1990, now U.S. Pat. No. 5,188,964.

The invention relates to a method of predicting disease-free survival in cancer patients based on overproduction levels of one or more stress response proteins from primary tumors. The method is particularly useful in predicting tumor recurrence in node-negative breast cancers.

Stress response proteins, srp's, have been recognized for several years, although in earlier terminology they were commonly called heat shock proteins, hsp's, because they were originally discovered as families of related proteins rapidly overproduced in divergent species in response to temperature stress. Subsequently these proteins were found to be induced in response to a variety of environmental stresses, including stimuli such as heat, heavy metals, toxins, drugs, hypoxia, and alcohol.

The precise function of stress response proteins is still largely a matter of speculation. It is widely assumed that these proteins protect cells from the effects of stress, but little is known about the mechanisms of induction and even less is understood about the relationships between number and amount of protein induced and the underlying physiological phenomenon.

There have been speculations that pretumorous or tumor cells might express increased amounts of stress response proteins, leading some workers to search for a relation between levels of these proteins and tumor manifestation. But although readily induced, the higher levels of heat stress proteins did not appear to relate to increased probability of tumor recurrence; in fact, some studies indicated that metastatic tumor burden generally decreased following induction of stress proteins (S. P. Tomasovic and D. R. Welch, *Hyperthermia* 2, 253 (1986)). Subsequent work by McGuire and colleagues, however, demonstrated that an estrogen-induced protein found in MCF-7 human breast cancer cells was identical to one of the earlier discovered heat shock proteins, hsp27, and that hsp27 might be associated with node-negative breast cancer patients at high risk of recurrence. Nevertheless, correlation factors were relatively weak and not sufficient to suggest a clinically useful method of prognostication.

The phenomenon of heat shock response was first observed nearly three decades ago by Ritossa (F. Ritossa, *Experientia* 18, 571 (1962)) who found that an increase in temperature from 20° to 37° C. as well as exposure to certain chemicals such as dinitrophenol or sodium salicylate, leads to a remarkable change in the puffing pattern of polytene chromosomes in salivary glands of fruit flies (*Drosophila busckii*). Nearly 12 years after this observation, Tissieres et al. (A. Tissieres, H. K. Mitchell, U. M. Tracy, *J. Mol. Biol.* 84, 389 (1974)) reported the induction of a set of proteins called heat shock proteins (hsp's), as a consequence of heat shock. Today, practically all types of organisms are known to respond to an increase in temperature in a basically similar fashion by massive synthesis and accumulation of a group of hsp's with almost no tissue or cell type specificity. Major hsp's are now known to be very highly conserved through evolution, strongly suggesting their vital role in survival of the organisms. Nearly all species induce the synthesis of proteins in the size ranges of 80 to 90 kDa, 68 to 74 kDa, and 18 to 30 kDa. In the past few years, the genes encoding the hsp's have been isolated and through sequence analysis have been placed into three "universal" families. These are known by their molecular weights: hsp90, hsp70, and hsp27 (the exact molecular weight differs slightly from organism to organism). These hsp genes contain a conserved sequence of 14 base pairs in the 5' noncoding region, the Pelham box, which serves as the promoter for hsp mRNA transcription. Recently, a relationship between the sequences of hsp's and another family of stress proteins, the glucose-regulated proteins (grp's), has been reported. These proteins are oversynthesized in response to glucose starvation. Two major grp's have been identified as grp94 and grp78.

Although the precise function of stress response proteins (srp's) is not known, they are thought to be intimately involved in enhancing the cell's ability to recover from stress (e.g. conferring thermotolerance). Yet the exact biochemical mechanism of this protection of cells against physical and chemical environmental insults remains a mystery. There are several excellent and comprehensive reviews on this subject including the organization and regulation of expression of hsp genes (S. Linquist, E. A. Craig, *Ann. Rev. Genet.* 22, 631 (1988); M. J. Schlesinger, *J. Cell Biol.* 103, 321 (1986); H. R. B. Pelham, *Cell* 46, 959 (1988); E. A. Craig, CRC *Crit. Rev. Biochem.* 18, 239 (1985)).

In 1980, a cytoplasmic, estrogen-induced protein of 24,000–28,000 Daltons molecular weight (termed "24K") in MCF-7 human breast cancer cells (D. P. Edwards, D. J. Adams, N. Savage, W. L. McGuire, *Biochem. Res. Commun.* 93, 804 (1980)) was reported. Its relative abundance in estrogen-stimulated MCF-7 cells enabled researchers to rapidly develop a highly specific monoclonal antibody against it (D. J. Adams, H. Hajj, D. P. Edwards, R. J. Bjercke, W. L. McGuire, *Cancer Res.* 43, 4297 (1983)). Nucleotide and deduced amino acid sequence of "24K" (S. A. W. Fuqua, M. B. Salingaros, W. L. McGuire, ibid. 4.9, 4126 (1989)) revealed its identity to the low molecular weight human heat shock protein hsp27, earlier reported in HeLa cells (E. Hickey et al., *Nucleic Acid Res.* 14, 4127 (1986)). Somatic cell hybridization showed that it is a multigene family, located on three different chromosomes namely 3,9 and X (S. McGuire, S. A. W. Fuqua, S. L. Naylor, D. A. Helen-Davis, W. L. McGuire, *Somatic Cell Genet.* 15, 167 (1989)). It is dually induced by heat shock as well as by estrogen in MCF-7 cells. A study of its possible significance for predicting clinical outcome showed that it was a factor for defining node-negative breast cancer patients at high risk of recurrence (G. C. Chamness, A. Ruiz, L. Fulcher, G. M. Clark, W. L. McGuire, *Breast Cancer Res. Treat.* 12, 130 (1988) (Abstract #94); G. C. Chamness et al., *Proc. Am. Assoc. Cancer Res.* 30, 252 (1989)) (Abstract #1002).

The heat shock protein hsp90 is known to interact with several protein-tyrosine kinases between the time of their synthesis and their ultimate association with the plasma membrane. The transforming protein of Rous Sarcoma Virus, pp60$^{src}$, was the first tyrosine kinase with which hsp90 was shown to have a specific association (J. S. Brugge, E. Erikson, R. L. Erikson, *Cell* 25, 363 (1981); H. Oppermann, W. Levinson, J. M. Bishop, *Proc. Natl. Acad. Sci.* 78, 1067 (1981)). Other transforming proteins with tyrosine kinase activity, yes, fps, fes, and fgr, also form stable complexes with a 90 kDa protein. In some cases this 90 kDa protein has been identified as hsp90 (B. Adkins, T. Hunter, B. M. Sefton, *J. Virol.* 43, 448 (1982); L. A. Lipsich, J. R. Cutt, J. S. Brugge, *Mol. Cell Biol.* 2, 875 (1982); and A. Ziemiecki, *Virology* 151, 265 (1986)). It has been proposed that hsp90 transports and modulates these kinases by forming soluble, inactive complexes. Hsp90 has also been found associated with other cellular kinases, e.g. heme-controlled eIF2-alpha kinase and casein kinase II (D. W. Rose, R. E. H. Wettenhall, W. Kudlicki, G. Kramer, B. Hardesty, *Biochemistry* 26, 6583 (1987)).

All steroid hormone receptors, including the estrogen, progesterone, and glucocorticoid receptors, can be isolated in the inactivated state (i,e,., in the absence of steroid hormones) as approximately 300 kDa complexes, which in addition to the specific hormone-binding proteins, contain 90 kDa proteins that have now been identified as hsp90 (M. G. Catelli, C. Radanyi, J. M. Renoir, N. Binart, E. E. Baulieu, *J. Cell Biochem. Suppl.* 12D, 286 (1988); J. J. Dougherty, R. K. Puri, D. O. Toft, *J. Biol. Chem.* 259, 8004 (1984); I. Joab, et al., *Nature* 308, 850 (1984); G. Redeuilh, B. Moncharmont, C. Secco, E.-E. Baulieu, *J. Biol. Chem.* 262, 6969 (1987); J.-M. Renoir, T. Buchou, E.-E. Baulieu, *Biochemistry* 25, 6405 (1986); and E. R. Sanchez, P. R. Housley, W. B. Pratt, *J. Steroid Biochem.* 24, 9 (1986)). Dissociation of hsp90 from the complex leads to the activation of the receptor for DNA binding (I. Joab, et al., *Nature* 308, 850 (1984); J.-M. Renoir, T. Buchou, E.-E. Baulieu, *Biochemistry* 25, 6405 (1986); and E. R. Sanchez, et al., *J. Biol. Chem.* 262, 6986 (1987)). In the absence of hsp90, the hormone-binding receptor will bind to the DNA whether hormone is present or not (E. R. Sanchez, et al., *J. Biol. Chem.* 262, 6986 (1987)). Hsp90 itself binds neither DNA nor hormone. Apparently, binding of hsp90 to the receptor prevents the receptor from binding to DNA until hormone disrupts association of hsp90 to the receptor.

In broad outline, hsp90 appears to play a role in steroid receptor complexes similar to that in tyrosine kinase complexes, keeping the receptor inactive until the proper signal for activation is received.

Recently, hsp90 has also been reported to associate with actin in lymphocyte extracts, in a manner dependent on calcium and regulated by calmodulin (S. Koyasu, et al., *Proc. Natl. Acad. Sci. U.S.A.* 83, 8054 (1986); and E. Nishida, S. Koyasu, H. Sakai, I. Yahara, *J. Biol. Chem.* 261, 16033 (1986)). It has been postulated that the actin association provides a mechanism for transport of hsp90. In this regard, and considering the tendency of hsp90 to move into the nucleus with heat shock, it is notable that actin filaments rearrange during heat shock and may even be found in substantial quantities in the nuclei of heat-shocked cells (W. J. Welch, J. P. Suhan, *J. Cell Biol.* 101, 1198 (1985)). Hsp90 also appears to be associated with tubulin both in vitro and in vivo (E. H. Bresnick, T. Redmond, E. R. Sanchez, W. B. Pratt, M. J. Welsh, *J. Cell Biochem. Suppl.* 12D, 283 (1988)). Given the high concentrations of actin, tubulin, and hsp90 in the cell, these associations may be biologically significant.

A tumor-specific transplantation antigen, Meth A, has also recently been identified as hsp90 (S. J. Ullrich, E. A. Robinson, L. W. Law, M. Willingham, E. Appella, *Proc. Natl. Acad. Sci. U.S.A.* 83, 3121 (1986)).

In humans, the heat shock protein hsp70 represents a multigene family, located on chromosomes 6, 14, 21, and at least one other chromosome (A. M. Goate, et al., *Mum. Genet.* 75, 123 (1987); and G. S. Harrison, et al., *Somatic Cell Mol. Genet.* 13, 119 (1987)). Their protein products are present in different cellular compartments and are often associated with other proteins. All bind ATP with high affinity (T. G. Chappell, et al., *Cell* 45, 3 (1986); W. J. Welch, J. R. Feramisco, *Mol. Cell. Biol.* 5, 1229 (1985); and M. Zylicz, J. H. LeBowitz, R. McMacken, C. P. Georgopoulos, *Proc. Natl. Acad. Sci. U.S.A.* 80, 6431 (1983)) and are implicated in a number of cellular processes. The major hsp70 is a cell cycle regulated protein (K. L. Milarski, R. Morimoto, *Proc. Natl. Acad. Sci. U.S.A.* 83, 9517 (1986)), is serum stimulated (B. J. Wu, R. I. Morimoto, *Proc. Natl. Acad. Sci. U.S.A.* 82, 6070 (1985)), and is induced by adenovirus E1A protein (J. R. Nevins, *Cell* 29, 913 (1982)).

It seems that the cell exploits a general property of the hsp70 family, namely the ability to disrupt protein-protein interactions, to perform specific tasks. Most of the "reactions" involving proteins of the hsp70 family require ATP. Probably the disruption of the protein-protein interactions uses the energy released on ATP hydrolysis.

One function of hsp70 may be the repair of damaged cells. Very shortly following heat shock, hsp70 translocates from cytoplasm to nucleus changing from a "soluble" cytosolic to an "insoluble" nuclear-matrix form. In the nucleus, it subsequently concentrates in nucleoli where it apparently binds to partially assembled ribosomes (W. J. Welch, J. P. Suhan, *J. Cell Biol.* 103, 2035 (1986)). Nucleoli are very sensitive to thermal damage, but transfection of cells with a plasmid that overproduces hsp70 accelerates their recovery from heat shock (H. R. B. Pelham, *EMBO J* 4, 3095 (1984)), indicating that hsp70 binds to denatured or abnormal proteins after heat shock to prevent their aggregation and thus to prevent cellular damage. Hsp70 is rapidly and completely released from "insoluble" nuclear matrix on addition of ATP (M. J. Lewis, H. R. B. Pelham, *EMBO* 4, 3137 (1985)). This observation led Lewis and Pelham (M. J. Lewis, H. R. B. Pelham, *EMBO J* 4, 3137 (1985)) to propose that hsp70 binds to denatured, aggregated proteins and solubilizes them. Energy from ATP hydrolysis subsequently causes hsp70 to release, thereby allowing the proteins to refold.

Clathrin-uncoating ATPase has been identified as a member of the hsp70 gene family. In the presence of ATP, an hsp70-like protein binds to the clathrin cages and is induced to hydrolyze ATP, resulting in the disruption of clathrin-clathrin interactions and finally in disassembly of the cage into clathrin trimers (J. E. Rothman, S. L. Schmid, *Cell* 46, 5 (1986); T. G. Chappell, et al., *Cell* 45, 3 (1986); and E. Ungewickell, *EMBO J* 4, a385 (1985)).

In *E. coli*, hsp70 is the product of the dnak gene, which encodes a protein that is 50% identical in amino acid sequence to hsp70 of eukaryotes (J. C. A. Bardwell, E. A. Craig, *Proc. Natl. Acad. Sci. U.S.A.* 81, 848 (1984)). Dnak protein interacts with lambda phage O and P proteins during phage replication (J. H. LeBowitz, C. Zylicz, C. Georgopoulos, R. McMacken, *Proc. Natl. Acad. Sci. U.S.A.* 82, 3988 (1985); and Dodson et al., *Proc. Natl. Acad. Sci. U.S.A.* 82, 4678 (1985)), again implicating hsp70 in the disruption of a tight protein-protein interaction. Like clathrin uncoating, this is an example of a specific function that exploits the general properties of the hsp70-like proteins.

In cells that overproduce the transformation-associated protein p53, stable complexes form between p53 and hsp70-related proteins (O. Pinhasi-Kimhi, D. Michalovitz, A. Ben-Zeev, M. Oren, *Nature* 320, 182 (1986)). Mutations in the gene encoding p53 that inactivate its tumor suppressing potential also result in the synthesis of mutant proteins which show preferential association with hsp70-like proteins and have an increased half-life (C. A. Findley, et al., *Mol. Cell. Biol.* 8, 531 (1988)). It is hypothesized that this interaction leads to a higher stability of p53, and the complex can be dissociated in vitro with ATP. Interestingly, p53 synthesized in *E. coli* is found in association with dnak protein (C. F. Clarke, et al., *Mol. Cell. Biol.* 8, 1206 (1988)).

Several eukaryotic cell DNA viruses, i.e., adenovirus (J. R. Nevins, *Cell* 29, 913 (1982)), herpes virus (E. L. Notarianni, C. M. Preston, *Virology* 123, 113 (1982)), and Simian Virus 40 and polyoma viruses (E. W. Khanjian, H. Turler, *Mol. Cell. Biol.* 3, 1 (1983)) activate synthesis of hsp70 early in infection. Newcastle Disease Virus, an RNA virus, induces hsp70 and hsp90 in infected chicken cells (P. C. Collins, L. E. Hightower, *J. Virol.* 44, 703 (1982)). Hsp70 itself is reported to have a protease activity (H. K. Mitchell, N. S. Petersen, C. H. Buzin, Proc. Natl. Acad. Sci. U.S.A. 82 4969 (1985)).

Two proteins related to hsp70 and hsp90 and regulated by glucose starvation have been identified as grp78 and grp94, respectively (A. S. Lee, J. Bell, J. Ting, *J. Biol. Chem.* 259, 4616 (1984); and R. P. C. Shiu, J. Pouyssegur, I. Pastan, *Proc. Natl. Acad. Sci. U.S.A.* 74, 3840 (1977)). Grp's are not normally heat-inducible, but are overproduced under a variety of other physiological stresses such as anoxia, paramyxovirus infection, and treatment of cells with glycosylation inhibitors (S. C. Chang, et al., *Proc. Natl. Acad. Sci. U.S.A.* 84, 680 (1987)) or the calcium ionophore A23187 (Lin et al., *Mol. Cell. Biol.* 6, 1235 (1986)). These proteins are abundant in secretory cells and are found associated with endoplasmic reticulum, and may possibly carry out the same functions as hsp's.

Grp78 is about 60% homologous to hsp70 and is identical to BiP (S. Munro, H. Pelham, *Cell* 46, 291 (1986)), a protein known to bind to the immunoglobulin heavy chains in pre-B cells that do not make light chains (Bole et al., *J. Cell Biol.*, 102, 1558 (1986)). This finding suggests that grp78 prevents the formation of heavy chain aggregate and thus helps the process of immunoglobulin assembly. Grp78 binds to the aberrant proteins to keep them soluble in the same way as hsp70 acts on heat-denatured nuclear proteins. For example, it associates with mutants of hemagglutinin of influenza virus that fail to assemble into a mature trimeric glycoprotein (M. J. Gething, K. McCammon, J. Sambrook, *Cell* 46, 939 (1986)). Mammalian cell lines with decreased amounts of grp78 show increased secretion of mutant proteins (A. Dorner, M. Krane, R. Kaufman, *J. Cell Biochem. suppl.* 12D, 276 (1988)).

Grp94 has been partially sequenced, showing that the protein is more than 50% homologous to yeast hsp90 and Drosophila hsp83 (P. K. Sorger, H. R. B. Pelham, *J. Mol. Biol.* 194, 341 (1987)). It is glycosylated, soluble in the absence of detergents, and is probably a luminal protein. The role of grp94 is even less understood than that of grp78.

There is also little information on the function of the low molecular weight hsp's. A stretch of 75 amino acids which are conserved among four small Drosophila hsp's is found to be 50% homologous to the B chain of mammalian lens alpha crystallins (H. Bloemendal, T. Berns, A. Zweers, H. Hoenders, E. L. Benedetti, *Eur. J. Biochem.* 24, 401 (1972); and T. D. Ingolia, E. A. Craig, *Proc. Natl. Acad. Sci. U.S.A.* 79, 2360 (1982)), suggesting that these hsp's may serve some kind of structural role. The Drosophila hsp's form large insoluble aggregates in a perinuclear region of the cell after prolonged heat shock (N. C. Collier, M. J. Schlesinger, *J. Cell Biol.*, 103, 1495 (1986); and L. Nover, K.-D. Scharf, D. Neumann, *Mol. Cell. Biol.* 3, 1648 (1983)), but these aggregates dissociate during cell recovery.

There is also an association of srp's with acquired drug resistance. Exposure of renal adenocarcinoma cells to heat shock or chemical stresses has shown that the major MDR1 gene promoter has heat shock elements and its expression (both mRNA and protein) is increased by these stresses, with a concomitant development of resistance to vinblastine (K.-V. Chin, S. Tanaka, G. Darlington, I. Pastan, M. M. Gottesman, *J. Biol. Chem.* 265, 221 (1990)). MDR1 RNA levels, however, did not change following stresses that normally induce grp's. Similarly, in Chinese hamster ovary cells, Shen et al. (J. Shen, et al., *Proc. Natl. Acad. Sci. U.S.A.* 84, 3278 (1987)) found that the induction of grp's did not change the level of MDR1-encoded P-glycoprotein. But these cells nevertheless acquired resistance to doxorubicin through an unknown mechanism. These observations suggest that some srp's may also be involved either indirectly or directly in conferring drug resistance to cells. In renal cells, MDR1-encoded P-glycoprotein may additionally protect cells from the effects of heat shock and chemical stresses.

More recently, Huot et al. (personal communication) found that transfection of Chinese hamster ovary cells with the hsp27 gene results in development of multidrug resistance. These studies indicate the role of a specific hsp in the phenomenon of multidrug resistance.

Prognosis in clinical cancer is an area of great concern and interest. It is important to know the aggressiveness of the malignant cells and the likelihood of tumor recurrence in order to plan the most effective therapy. Breast cancer, for example, is managed by several alternative strategies. In some cases local-regional and systemic radiation therapy is utilized while in other cases mastectomy and chemotherapy or mastectomy and radiation therapy are employed. Current treatment decisions for individual breast cancer patients are frequently based on (1) the number of axillary lymph nodes involved with disease, (2) estrogen receptor and progesterone receptor status, (3) the size of the primary tumor, and (4) stage of disease at diagnosis (G. M. Clark et al., *N. Engl. J. Med.* 309, 1343 (1983)). It has also been reported that DNA aneuploidy and proliferative rate (percent S-phase) can help in predicting the course of disease (L. G. Dressler et al., *Cancer* 61, 420 (1988); and G. M. Clark et al., *N. Engl. J. Med.* 320, 627 (1989)). However, even with these additional factors, we are still unable to accurately predict the course of disease for all breast cancer patients. There is clearly a need to identify new markers, in order to separate patients with good prognosis who will need no further therapy from those more likely to recur who might benefit from more intensive treatments.

This is particularly true in the case of breast cancer which has not progressed to the axillary lymph nodes. There is now evidence in prospective randomized clinical trials that adjuvant endocrine therapy and adjuvant chemotherapy beginning immediately after surgical removal of the primary breast tumor can be of benefit in some of these node-negative patients. This has led to official and unofficial recommendations that most if not all node-negative breast cancer patients should be considered for some form of adjuvant therapy. But since the majority (~70%) of these patients enjoy long-term survival following surgery and/or radiotherapy without further treatment, it may be inappropriate to recommend adjuvant therapy for all of these patients. If there were sufficiently good methods to distinguish those node-negative patients who are "cured" from those destined to recur, only the latter should be treated. Thus, there is a great need for a general method of predicting tumor recurrence in these patients and in cancer patients in general once the primary tumor is detected.

The present invention seeks to address one or more of the foregoing problems in predicting tumor recurrence when the mere presence of an unusual protein is insufficient to reliably predict a present or potential disease state. It has been found that the number and "overproduction" levels of stress response proteins in primary tumor tissue show an unexpected and surprisingly high correlation with tumor recurrence. Consequently, the present work represents a significant advancement in cancer management because early identification of patients at risk for tumor recurrence will permit aggressive early treatment with significantly enhanced potential for survival.

It should be recognized that stress response proteins (srp's) are a class of proteins of which the previously recognized heat shock proteins (hsp's) are a subclass, and the glucose response (or glucose regulated) proteins (grp's) are another subclass. Since the hsp's respond to many stresses besides heat, there is a trend toward using the generic designation srp's for these proteins. In the present invention, srp's will refer to the class, while specific proteins will be given their original designations (e.g. hsp27).

The stress response proteins used in one embodiment of the invention are heat shock proteins 27, 70 and 90 and glucose response protein 94. These are known in the art as members of families of proteins having molecular weights in humans in the range of 27,70,90 and 94 kDa respectively. It is intended that stress response proteins refer to any stress response protein produced in the tumor cell for which it would be possible, using the method of the present invention, to determine "overproduction" levels. As yet undiscovered or untested stress response proteins would also be expected to be correlated with tumor recurrence since they are produced in response to the same stresses that result in hsp27, 70, 90 and/or grp94 overproduction. Up to four stress response proteins have been associated with tumor recurrence, but since correlation increases with the number of stress response proteins, it is expected that detection of additional stress response proteins will further improve correlation.

In one embodiment of the invention, the presence of two or more of these proteins can be correlated with tumor recurrence. However, generally the mere presence of the proteins is relatively weakly associated with tumor recurrence only when several of the proteins are detected, for example, when four srps are present. Stronger correlations have been found when the levels of the proteins exceed "overproduction" levels. Such "overproduction" is not typically calculated in terms of absolute protein levels, but is determined using relative measurements. These relative measurements are illustrated for quantitation purposes with an "internal standard"; however, it will be appreciated that other standards or methods of determination may be used, such as comparison external standards, hsp mRNA measurements, or absolute values.

One measure of relative value of "overproduction" is to determine relationships of tumor sample stress response protein levels to basal level of stress response proteins produced by a cultured cell line. Most cultured cells produce srps, probably because of particular stresses imposed by culture conditions. Normal cells, cancer cells, or genetically altered cells could be used. Although human cells are preferred, bacterial, yeast, other mammalian cells or the like also produce similar stress-induced proteins which in fact often show significant homology with human stress-induced counterparts (Watowich, S. S. and Morimoto, R. I., Mol. Cell. Biol 8, 393–404 (1988)). Cells particularly sensitive to stress are preferred, while breast cancer cells have been particularly useful. A most preferred cell line is a standard breast tumor cell line on deposit with the American Type Culture Collection (ATCC, MCF-7).

A basis for one aspect of the present invention is the inventors' finding that "overproduction" levels of stress response proteins are associated with tumor recurrence. When a stress response protein exceeds a determined basal level, it has been found to become a significant factor in tumor recurrence. It is important to recognize that basal levels are not the levels of srps found in cultured cell lines used to provide internal standards; rather, these are amounts of srps which may be found in tumor cells that do not cause tumor recurrence. It is, for example, possible that an "overproduced" tumor sample stress response protein will have a relatively lower level than the corresponding srp in the internal standard. When tumor cell determined basal levels are exceeded, the stress response is "overproduced" and indicates increased risk of tumor recurrence. On the other hand, the mere presence, without overproduction, of one or more stress response proteins is rarely correlated with higher risk of tumor recurrence.

Overproduction is related to a level of srp's above a determined low or basal level and is different for each srp. Thus, in this invention a level of each protein is identified as a "cutoff" value, above which there is a significant correlation between the presence of the srp and tumor recurrence. Some "cutoff" values are not sharp in that clinical correlations are still significant over a range of values on either side of the cutoff; however, it is possible to select an optimal cutoff value for each stress response protein. The cutoff value used for a given application is termed the "cutpoint".

Generally, overproduction of several stress response proteins provides higher correlations with tumor recurrence than overproduction of one or two stress response proteins. In one embodiment of the invention, any one of grp94, hsp70 or hsp90 may be used to correlate tumor recurrence with overproduction levels. In a preferred embodiment, any two or three of hsps selected from hsp70, hsp90, hsp27 or grp94 may be used. In a most preferred embodiment, overproduction levels of hsp27, hsp70, hsp90 and grp94 are measured.

Measurement of levels of grp94 and three hsp's (hsp90, hsp70, and hsp27) in a large cohort of well characterized human primary breast tumors with extensive clinical followup, has demonstrated that overproduction of these proteins occurs relatively frequently in breast cancer, and, surprisingly, with considerable correlation among the four srp's. Furthermore, higher levels of all (grp94 marginally) are associated with tumor recurrence behavior in breast cancer patients having no tumor extensions to the axillary lymph nodes at primary treatment. Simultaneous occurrence of more than one srp is a more powerful predictor of poor disease-free survival; the higher the number of overproduced srp's, the greater is the risk of tumor recurrence.

A relative measure of "overproduction" is used in the practice of this invention. The units defining "overproduction" are relative to an arbitrarily assigned cancer cell line standard. In a preferred embodiment, MCF-7 human breast cancer cells (ATCC-HTB22 MCF-7) are grown under defined conditions. Aliquots of homogenized cells are analyzed along with each set of samples of test tissue by standard procedures. Each $\mu$g protein aliquot of MCF-7 cells is arbitrarily assigned a "one unit" value so that the level of any given stress response protein in the test sample is measured in units against this standard MCF-7 cell unit. Absolute values of the arbitrary "units" can be readily determined by one skilled in the art. It should be appreciated that the "overproduction" values selected are illustrative and that correlations may still exist between levels of stress response proteins falling somewhat below the given cutoff values and tumor recurrence. Selection of the cutoff values is determined by statistical considerations and does not imply an absolute value.

Correlations were determined by well known multivariate analysis techniques. Different statistical treatment could be used to define other sets of values for the stress response proteins which could improve correlations. For example, if improved correlations were found, overproduction values would differ somewhat from the cutoff values defined in the present invention. In the present invention, ranges of values were determined for each stress response protein. In a preferred embodiment, optimal cutoff levels of the stress response proteins hsp27, 70, and 90 and grp94 are 126, 217, 32, and 45 units per 100 $\mu$g tumor protein. Above these levels, the proteins are considered overproduced and hence indicative of significant risk of tumor recurrence. It is understood that improvements in optimal cutoff values could be determined, depending on the sophistication of statistical methods used and on the number and source of samples used to determine basal values for the different hsps.

The stress response proteins useful in the practice of this invention are typically produced in response to cell stress. The four used in the present invention are the best known, but others have been discovered and are contemplated as being included in the invention. It is likely, for example, that grp78, another glucose response protein, will exhibit correlation with tumor recurrence when overproduced in cancer tissue. The details of measurement and correlation of grp78 would be analogous to those used in the present invention to determine overproduction of grp94 and hsp's 27, 70 and 90.

In preferred practice of the invention, hsps are extracted from tumor cell tissue. However, it should also be possible to measure levels of these proteins in the serum. Tumors are known to readily shed cells and, after release into the bloodstream might be expected to burst due to cell fragility. Thus detection of any hsps present could be used to develop overproduction correlations in a manner analogous to that demonstrated with the tissue samples. Very small quantities of hsps might be measured, for example, using antibodies directed to the particular hsps.

Immunologically based diagnostic kits for determining the number and levels of stress response proteins in tissue samples are contemplated. Such kits would include the appropriate anti-srp antibody together with an immunoreaction detection reagent. As used herein, an immunoreaction detection reagent is a reagent capable of detecting or indicating a specific immunoreaction between the antibody and the hsp antigen. Examples of such reagents include enzyme, fluorescent or radiolabeled antigens or antibodies. Many such reagents and their use are well known to those of skill in the art. Some of the methods of detection utilizing immunoreactions include Western blot, immunohistochemical procedures and ELIZA assays. These methods are also well known to those skilled in the art.

An example of kit components would include a stress response protein standard with several stress response proteins, antibodies (preferably monoclonal) to each stress response protein, a negative control and a positive control. An example of a control is a breast tumor extract, but other standards could be used, including synthetic standards prepared from synthesis of all or part of the srps of interest. Tumor cell extracts are preferable, however, as the presence of other cell components would more closely mimic the sample. For convenience, these components may be supplied in lyophilized form.

Several variations of kits based on antibody binding are envisioned. For example, use of a second antibody specifically directed against the first antibody in a sandwich type detection system can be used in well-known variations of the ELISA technique. Detection of second antibodies tagged with various labels, including radioisotopes, chromophores, enzymes, and the like could also be used. Another variation is the binding of an antibody, for example a monoclonal antibody, by a second biotinylated antibody followed by reaction with an avidin biotinylated horseradish peroxidase complex. If the first antibody is attached to a substrate such as an agarose bead or a microtiter plate well, the color developed can be quantitated relative to a standard supplied in the kit.

Although the applications of the invention which are described here are based on antibodies specific for each srp, it will be understood by those in the art that the level of each srp is related to the level of the messenger RNA (mRNA) which encodes it. Therefore, when the amino acid sequence of the srp is known, methods can easily be envisioned by which srp overproduction in tumors would be determined by measuring levels of the corresponding mRNA's. Rather than antibodies, complementary DNA's for each srp mRNA would be the specific recognition elements, and the existing techniques known as Northern blots, slot blots, in situ hybridizations, and polymerase chain reactions (PCR) would be applied. Messenger RNA levels have been used to determine production of corresponding proteins (G. Bevilacqua, M. E. Sobel, L. A. Liotta and T. S. Steeg, *Cancer Res.* 49, 5185–5190 (1989)). Amino acid sequences, and consequent cDNA preparation, for several of the srps are known, including hsp70 (Watowich, S. S. and Morimoto, R. I., Mol. Cell. Biol., 8, 393–405 (1988)), hsp90 (Hickey, L., Brandon, S. E., Smale, G., Lloyd, D. and Weber, L. A., Mol Cell 9, 2615–2625 (1989)) and hsp27 (Hickey, et al., Nucleic Acids Res. 14, 4127–4145 (1986).

Figure 1:
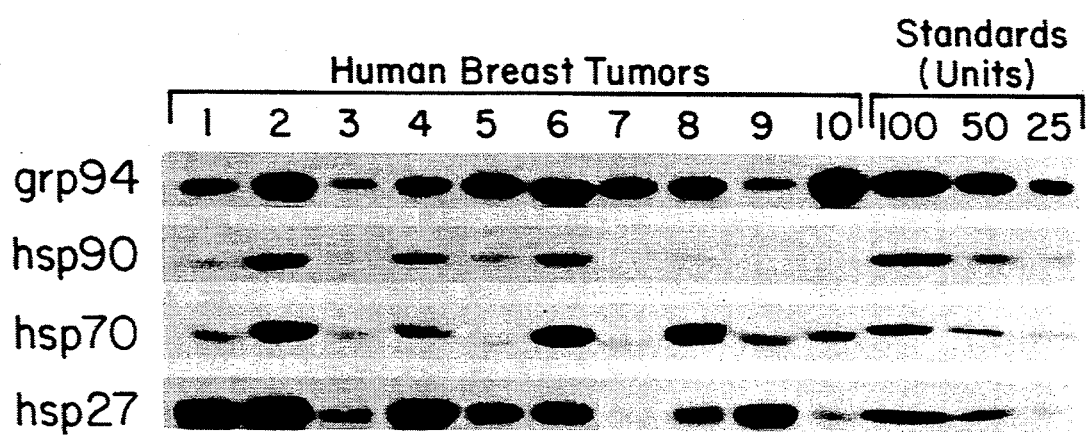
FIG. 1 shows a Western Blot analysis of ten human breast tumor extracts using monoclonal antibodies to hsp27, hsp70, hsp90, and grp94. An internal reference standard of an MCF-7 human breast cancer cell protein extract is shown as the standard against which relative units were calculated.
Figures 2A, 2B:
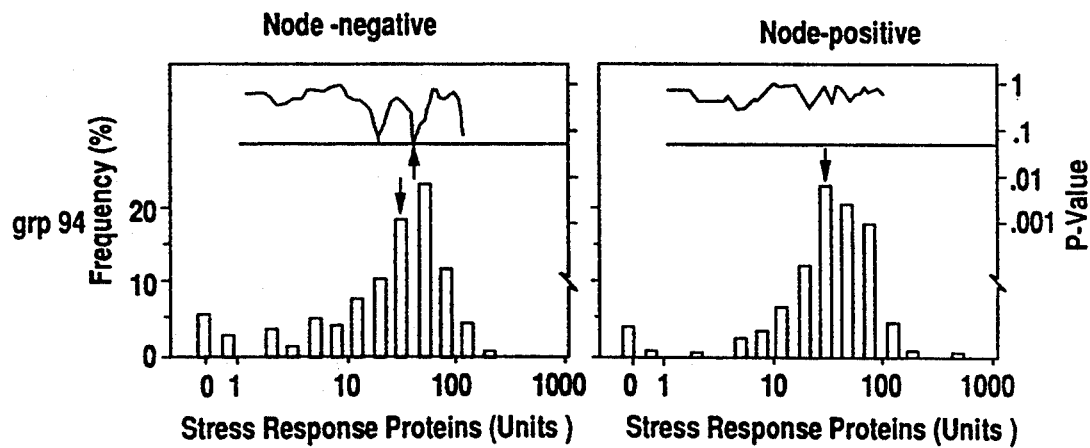
FIGS. 2A, 2B, 2C, 2D, 2E, 2F, 2G and 2H are a series of graphs showing distributions of stress response proteins in node-negative and node-positive breast cancer patients, and the statistical significance of the full range of possible cutoff values for each srp in predicting recurrence.
Figures 2C, 2D:
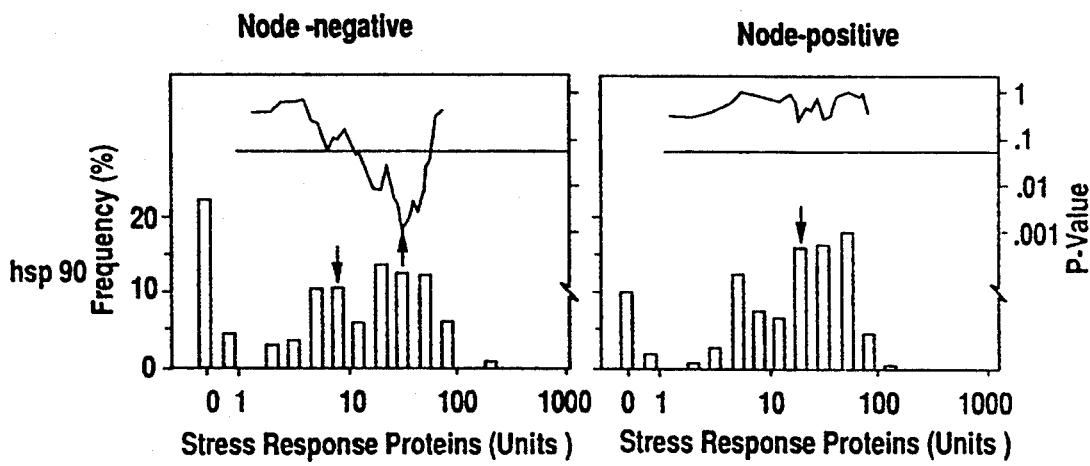
Figures 2E, 2F:
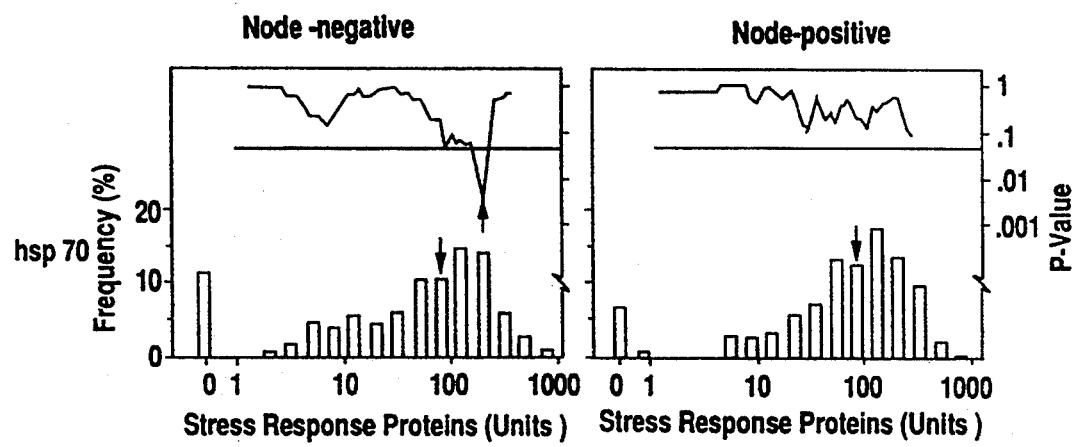
Figures 2G, 2H:
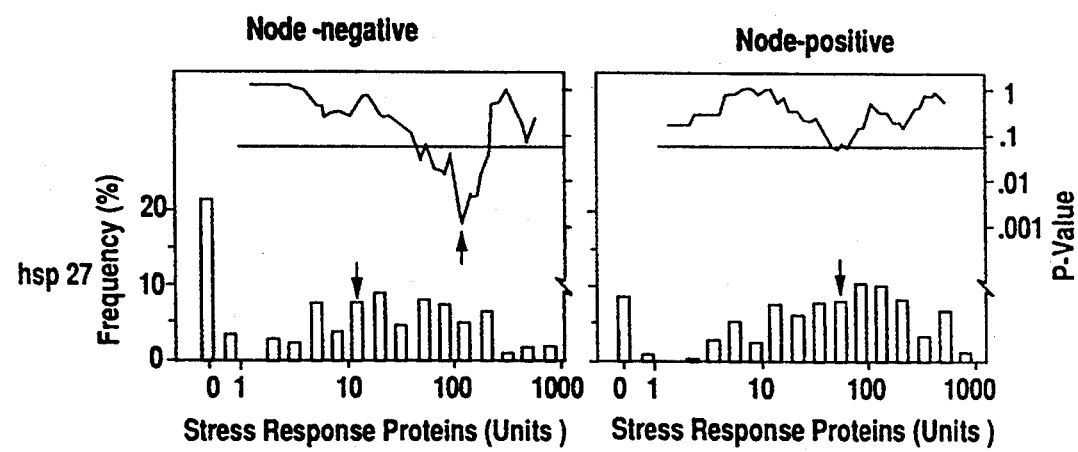
Figure 3B:
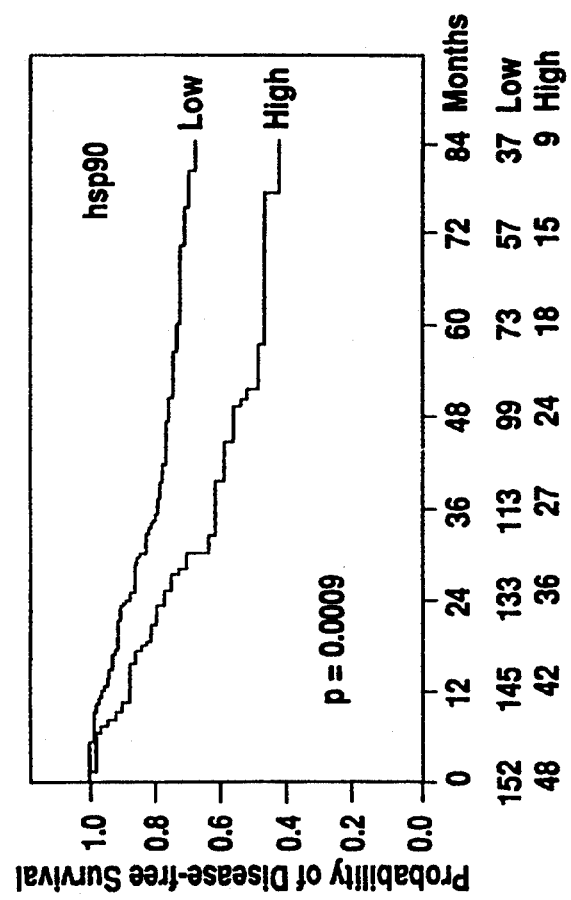
FIGS. 3A, 3B, 3C and 3D show the association of stress response proteins with tumor recurrence for node-negative breast cancer patients using a Kaplan-Meier analysis of time to recurrence.
Figure 3A:
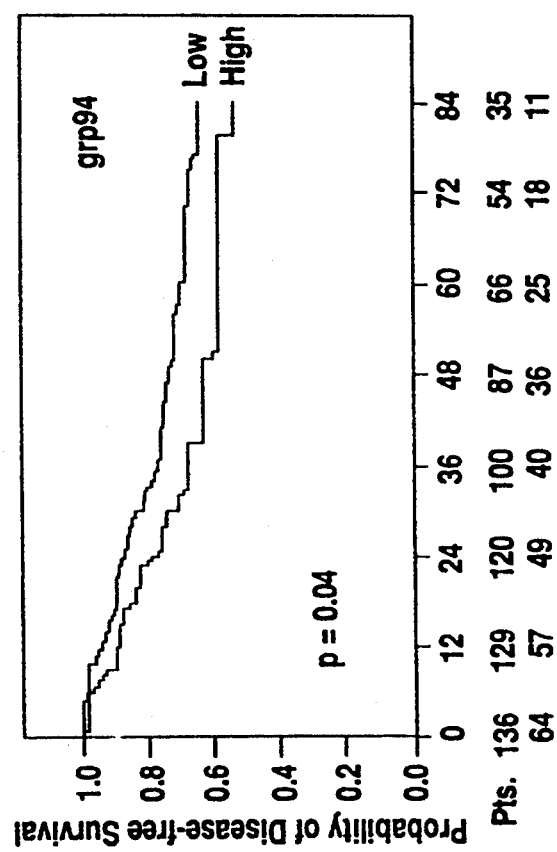
Figure 3D:
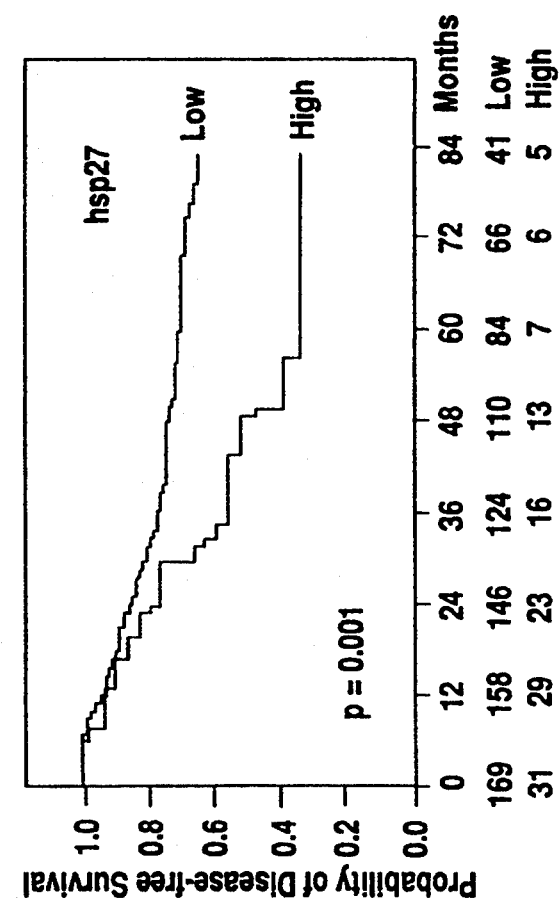
Figure 3C:
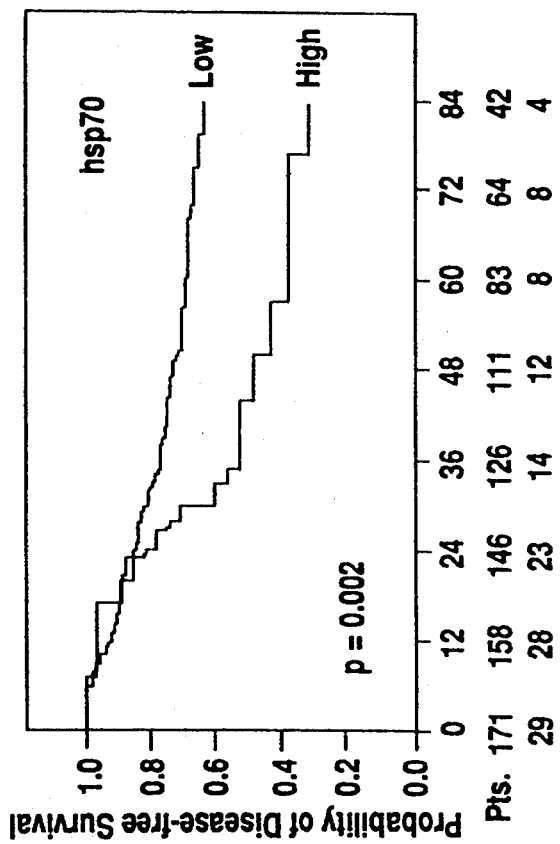

The present invention allows prediction of survival or tumor recurrence in cancer patients based on a determination of one or more stress response proteins (srps) in a tumor sample. The mere presence of these srps in tumor tissue has little prognostic value; however, surprisingly, when one or more srp exceeds a determined basal level in the tumor tissue, good correlations with tumor recurrence have been found. Further, in another unexpected finding, the greater the number of "overproduced" srps, the better the correlation with long-term (greater than five years) survival.

The method is described here in detail for determination of "overproduction" in breast tumor samples using a relative measure of srps. The relative measure is based on comparison with srp production in cultured cells, but one will appreciate that there is some absolute amount of these srps above which there is a high risk of cancer recurrence. This amount could be measured in absolute concentrations and is not necessarily dependent on the relative "internal standard" method of measurement used to illustrate one embodiment of the invention. The numbers obtained using a particular breast cancer cell line to determine "overproduction" will therefore be different from overproduction numbers and cutoff values obtained when other cell comparison standards are used or if absolute values are determined.

In order to detect and measure srps in human cancers, frozen, stored tumor tissues from 398 primary breast cancers were analyzed for four srp's by a semi-quantitative Western Blot procedure in a blinded fashion, i.e. without prior knowledge of any tumor characteristics or disease outcome. Tissues for the quantitation of these proteins were obtained from the biopsy specimens. Values for estrogen receptor (ER), progesterone receptor (PgR), HER-2/neu oncogene protein (a growth factor receptor-like transmembrane glycoprotein of 185 kDa) (A. K. Tandon, G. M. Clark, G. C. Chamness, A. Ullrich, W. L. McGuire, J. Clin. Oncol. 7, 1120 (1989)), DNA ploidy (a measure of DNA content) (L. G. Dressier, L. C. Seamer, M. A. Owens, G. M. Clark, W. L. McGuire, Cancer 61, 420 (1988)), and the 34 kDa mature form of cathepsin D (an estrogen-induced lysosomal acidic protease) (A. K. Tandon, G. M. Clark, G. C. Chamness, J. M. Chirgwin, W. L. McGuire, N. Engl. J. Med. 322, 297 (1990)) were available on the tumor specimens analyzed.

To account for the variability in content of tumor cells in different regions within the same specimen, in the first step breast tumors were mechanically pulverized in liquid nitrogen to obtain a uniform distribution of tumor cells. To further minimize the potential risk of uneven dilution of tumor cell proteins with stromal proteins, larger quantities (100 mg) than needed (10 mg) were used for protein extraction. Total proteins were extracted with sodium dodecyl sulfate (A. K. Tandon, G. M. Clark, G. C. Chamness, A. Ullrich, W. L. McGuire, J. Clin. Oncol. 7, 1120 (1989)).

One hundred micrograms of extracted proteins were subjected to Western Blot analysis using monoclonal antibodies to grp94 (D. P. Edwards, N. L. Weigel, W. T. Schrader, B. W. O'Malley, W. L. McGuire, Biochem. 25, 4427 (1984); and D. R. Sargan, M.-J. Tsai, B. W. O'Malley, Biochem. 25, 6252 (1986); the monoclonal antibody 9G10 used here reacts with purified grp94 in Western Blot assay, unpublished observation from W. J. Welch's laboratory), hsp90 (S. Schuh et al., J. Biol. Chem. 260, 14292 (1985)), hsp70 (a gift from W. J. Welch), and hsp27 (D. J. Adams, H. Hajj, D. P. Edwards, R. J. Bjercke, W. L. McGuire, Cancer Res. 43, 4297 (1983)).

Remaining tumor protein extracts were immediately frozen and stored at $-70°$ C. Examples of ten tumors along with an internal reference standard of MCF-7 human breast cancer cells (see below) are shown in FIG. 1. The levels of these srp's in individual tumors were calculated in relative units per one hundred micrograms tumor protein by the ratio of the integrated signal in the tumors relative to the MCF-7 internal standard.

The stress response proteins in tumors were measured against the content of the same stress response proteins in a cell culture of human breast cancer cells. These cells were originally obtained from the Michigan Cancer Foundation, and can be purchased from the American Type Culture Collection (ATCC HTB22 MCF-7). In preferred practice the cells are cultured in Eagle's minimum essential medium supplemented with non-essential amino acids, gentamycin, calf serum, L-glutamine and bovine insulin at near physiological pH, as specified in Example 5.

A second step was to compare the levels of each srp with cancer recurrence. Levels of all four srp's ranged from undetectable to high. Actual ranges per 100 $\mu$g tumor proteins were 0–557 units for grp94; 0–173 units for hsp90; 0–862 units for hsp70; and 0–2645 units for hsp27. Distributions of the four srp's under study for node-negative and node-positive breast cancer patients are shown in FIG. 2. The distributions for these srp's in both groups were approximately log-normal. Median values of srp's in node-positive versus node-negative breast tumors were as follows: 37 vs 32 for grp94 ($P=0.2$); 20 vs 10 for hsp90 ($P=0.001$); 82 vs 66 for hsp70 ($P=0.08$); and 48 vs 14 for hsp27 ($P<0.0001$).

Correlations of the srp's with clinical manifestations of breast cancer disease and its ultimate outcome were determined. Conventionally, the median value of a given parameter is used to distinguish patients with high levels of the parameter from those with low levels. However, median values of all four srp's failed to discriminate these patients into low and high risks of disease recurrence. Therefore, a biologically meaningful cutoff value was sought for different srp's to distinguish patients at high risk of relapse. A wide range of cutoff values gave statistically significant separation of disease-free survival probabilities in the group of 200 node-negative patients (74 months median followup for patients still alive) for hsp90 (12 to 59 units), hsp70 (120 to 250 units), and hsp27 (46 to 232 units) (FIG. 2). For grp94, unlike hsp's, there was only one single cutpoint at 45 units. The optimum cutpoints for hsp90, hsp70, and hsp27 were 32, 217, and 126 units, respectively. For 198 node-positive patients the median followup was 61 months for patients still alive; however, in contrast to node-negative patients, no cutpoints gave a significant segregation of low and high risk patients for tumor recurrence (hsp27 marginally reached statistical significance but the apparent cutpoint range was extremely limited, FIG. 2).

The interrelationship of four srp's in node-negative breast tumors was determined. Tumors were classified as low or high using the optimum cutpoint for each srp. About fifty percent (101/200) of the tumors were found to contain low levels of all four srp's, leaving 50% as high for either one, two, three, or all four srp's. Only 2.5% (5/200) of tumors contained high levels of all four srp's. Therefore, though these four srp's were significantly correlated to each other, all were not concomitantly overproduced in all tumors, perhaps reflecting the diverse nature of physiological stress from tumor to tumor. Using the optimum cutpoints, 33.5% of tumors were high for grp94; 24% for hsp90; 15% for hsp70; and 15.5% for hsp27; either alone or in various combinations with the other three srp's. Data on overlapping incidence of srp's are shown in Table 1, and the correlation values are given in Table 2. A higher incidence of high levels of hsp90 and grp94 indicates that these srp's may be more sensitive indicators of the biological stress.

TABLE 1

Interrelationship of Four Stress Response Proteins with Each Other

| % Positive for: | Which are also Positive for: | | | |
|---|---|---|---|---|
| | grp94 | hsp90 | hsp70 | hsp27 |
| grp94 | 100 | 50 | 16 | 17 |
| hsp90 | 67 | 100 | 29 | 35 |
| hsp70 | 34 | 48 | 100 | 55 |
| hsp27 | 35 | 55 | 52 | 100 |

All pairwise comparisons were statistically significant (P < 0.05).
Spearman rank correlation coefficients (r) among these four srp's were all statistically significant (P < 0.05) and varied from 0.32 to 0.67 (see Table 2).

TABLE 2

Spearman Rank Correlation Coefficients (r) for the Pairwise Interrelationship of Four Stress Response Proteins With Each other

| | grp 94 | hsp90 | hsp70 | hsp27 |
|---|---|---|---|---|
| grp94 | | | | |
| hsp90 | 0.67 | | | |
| hsp70 | 0.44 | 0.61 | | |
| hsp27 | 0.32 | 0.50 | 0.63 | |

All pairwise comparisons were statistically significant (P < 0.05).

Association of srp's with other tumor characteristics which are biological indicators of metastatic potential, hormone responsiveness, or relative histopathologic differentiation was investigated. Data are summarized in Tables 3A and 3B. All four srp's were directly associated with high levels of cathepsin D, an estrogen-induced lysosomal protease supposed to be a marker of metastatic potential (hsp27 failed to reach statistical significance). Similar results were found using cathepsin D directly as a clinical discriminator in these sets of node-negative and node-positive patients (A. K. Tandon, G. M. Clark, G. C. Chamness, J. M. Chirgwin, W. L. McGuire, N. Engl. J. Med. 322, 297 (1990)).

In addition to cathepsin D, the following correlations/associations were observed: hsp27 and hsp70 with estrogen and progesterone receptor status; hsp90 and grp94 with aneuploidy; hsp70, hsp90, and grp94 with nuclear grade; and hsp27 and hsp90 with HER-2/neu oncogene protein. No significant correlations were found with tumor size or patient age.

The data in Tables 3A and 3B were obtained by analysis of tumors from 398 breast cancer patients ranging in age from 26 to 82 years with a median of 58 years. Tumor grp94≥45 units; hsp90≥32 units; hsp70≥217 units; and hsp27≥126 units per 100 µg of total tumor proteins were categorized as high (positive). Nodal status was considered negative when no lymph nodes contained tumor cells and positive if one or more nodes showed the presence of malignant cells. Tumor size (largest diameter) was recorded at the time of surgery. Levels of estrogen receptor (ER) and progesterone receptor (PgR) in fresh tumor cytosols were determined by standard methods (W. L. McGuire, M. De La Garza, G. C. Chamness, Cancer Res. 37, 637 (1977); B. Powell, R. E. Garola, G. C. Chamness, W. L. McGuire, ibid, 39, 1678 (1979)) and are expressed as fmoles per mg cytosolic proteins. Ploidy (DNA content) was determined by flow cytometric analysis (L. G. Dressier, L. C. Seamer, M. A. Owens, G. M. Clark, W. L. McGuire, Cancer 61, 420 (1988)). Levels of the HER-2/neu oncogene protein and the 34 kDa mature form of cathepsin D were quantitated by Western blotting and densitometry methods (A. K. Tandon, G. M. Clark, G. C. Chamness, A. Ullrich, W. L. McGuire, J. Clin. Oncol. 7, 1120 (1989); A. K. Tandon, G. M. Clark, G. C. Chamness, J. M. Chirgwin, W. L. McGuire, N. Engl. J. Med. 322, 297 (1990)). Analysis of data for association between srp's and other characteristics in breast cancer was performed using two-way contingency tables and nonparametric correlation coefficients.

TABLE 3A

Relationship Between Stress Response Proteins and Other Clinical Characteristics in Node-Negative Breast cancer

| Characteristic n | grp94 | | hsp90 | | hsp70 | | hsp27 | |
|---|---|---|---|---|---|---|---|---|
| | % grp+ | P | % hsp+ | P | % hsp+ | P | % hsp+ | P |
| Cathepsin D | | | | | | | | |
| < 75 units | 136 | 24 | 17 | | 9 | | 13 | |
| | | 0.0006 | | 0.0006 | | 0.009 | | 0.09 |
| ≧5 units | 64 | 48 | 39 | | 27 | | 22 | |

TABLE 3A-continued

Relationship Between Stress Response Proteins and Other Clinical Characteristics in Node-Negative Breast cancer

| Characteristic | n | grp94 % grp+ | P | hsp90 % hsp+ | P | hsp70 % hsp+ | P | hsp27 % hsp+ | P |
|---|---|---|---|---|---|---|---|---|---|
| Nuclear Grade | | | | | | | | | |
| 1 | 6 | 33 | | 0 | | 0 | | 0 | |
| 2 | 103 | 28 | 0.06 | 18 | 0.002 | 12 | 0.08 | 14 | 0.21 |
| 3 | 70 | 46 | | 40 | | 23 | | 21 | |
| Histologic Grade | | | | | | | | | |
| 1 | 6 | 33 | | 0 | | 0 | | 0 | |
| 2 | 111 | 30 | 0.12 | 24 | 0.17 | 14 | 0.39 | 17 | 0.54 |
| 3 | 62 | 45 | | 32 | | 19 | | 16 | |
| Estrogen Receptor | | | | | | | | | |
| ≧3 fmol/mg | 142 | 30 | 0.25 | 26 | 0.29 | 18 | 0.02 | 18 | 0.09 |
| <3 fmol/mg | 58 | 38 | | 19 | | 5 | | 9 | |
| Progesterone Receptor | | | | | | | | | |
| ≧5 fmol/mg | 99 | 27 | 0.16 | 23 | 0.80 | 24 | 0.0001 | 20 | 0.07 |
| <5 fmol/mg | 101 | 37 | | 25 | | 5 | | 11 | |
| Tumor Size | | | | | | | | | |
| ≦2 cm | 73 | 30 | 0.67 | 21 | 0.39 | 18 | 0.31 | 12 | 0.35 |
| >2 cm | 127 | 33 | | 26 | | 13 | | 17 | |
| Ploidy | | | | | | | | | |
| Diploid | 72 | 24 | 0.03 | 14 | 0.008 | 10 | 0.12 | 13 | 0.31 |
| Aneuploid | 116 | 39 | | 31 | | 18 | | 18 | |
| Age | | | | | | | | | |
| ≧50 years | 137 | 33 | 0.71 | 27 | 0.14 | 18 | 0.07 | 15 | 0.92 |
| <50 years | 63 | 30 | | 17 | | 8 | | 16 | |
| HER-2/neu | | | | | | | | | |
| <100 units | 171 | 32 | 0.66 | 21 | 0.01 | 16 | 0.23 | 13 | 0.04 |
| ≧100 units | 28 | 36 | | 43 | | 7 | | 29 | |

TABLE 3B

Relationship Between Stress Response Proteins and Other Clinical Characteristics in Node-Positive Breast Cancer

| Characteristic | n | grp94 % grp+ | P | hsp90 % hsp+ | P | hsp70 % hsp+ | P | hsp27 % hsp+ | P |
|---|---|---|---|---|---|---|---|---|---|
| Cathepsin D | | | | | | | | | |
| <75 units | 101 | 64 | 0.001 | 30 | 0.19 | 15 | 0.51 | 22 | 0.08 |
| ≧75 units | 98 | 85 | | 39 | | 18 | | 33 | |
| Estrogen Receptor | | | | | | | | | |
| ≧3 fmol/mg | 142 | 75 | 0.89 | 35 | 0.94 | 21 | 0.007 | 35 | 0.0002 |
| <3 fmol/mg | 57 | 74 | | 34 | | 5 | | 9 | |
| Progesterone Receptor | | | | | | | | | |
| ≧5 fmol/mg | 100 | 76 | 0.60 | 34 | 0.92 | 24 | 0.005 | 36 | 0.005 |
| <5 fmol/mg | 99 | 73 | | 35 | | 9 | | 18 | |
| Tumor Size | | | | | | | | | |
| <2 cm | 34 | 76 | 0.76 | 26 | 0.29 | 12 | 0.41 | 32 | 0.45 |
| ≧2 cm | 165 | 74 | | 36 | | 18 | | 26 | |
| Age | | | | | | | | | |
| ≧50 years | 129 | 74 | 0.98 | 37 | 0.34 | 21 | 0.03 | 30 | 0.18 |
| <50 years | 70 | 74 | | 30 | | 9 | | 21 | |
| HER-2/neu | | | | | | | | | |
| <100 units | 163 | 36 | 0.21 | 32 | 0.10 | 18 | 0.07 | 30 | 0.07 |
| ≧100 units | 34 | 50 | | 47 | | 6 | | 15 | |
| No. of Positive Nodes | | | | | | | | | |
| 1-3 | 74 | 39 | 0.82 | 38 | 0.42 | 14 | 0.37 | 28 | 0.76 |
| >3 | 125 | 38 | | 32 | | 18 | | 26 | |

The association of each srp with the likelihood of development of recurrent breast cancer was studied. Kaplan-Meier analyses of time to recurrence for the node-negative patients are shown in FIG. 3. Patients with higher levels of grp94, hsp90, hsp70, or hsp27 in primary tumors were at a greater risk of developing early recurrent cancer compared to those with lower levels of these proteins.

Both hsp27 and hsp70 distinguished patients with different recurrence rates within 18 months of surgical removal of tumor. Hsp90 separated the two groups of patients within a few months of primary treatment.

Figure 4:
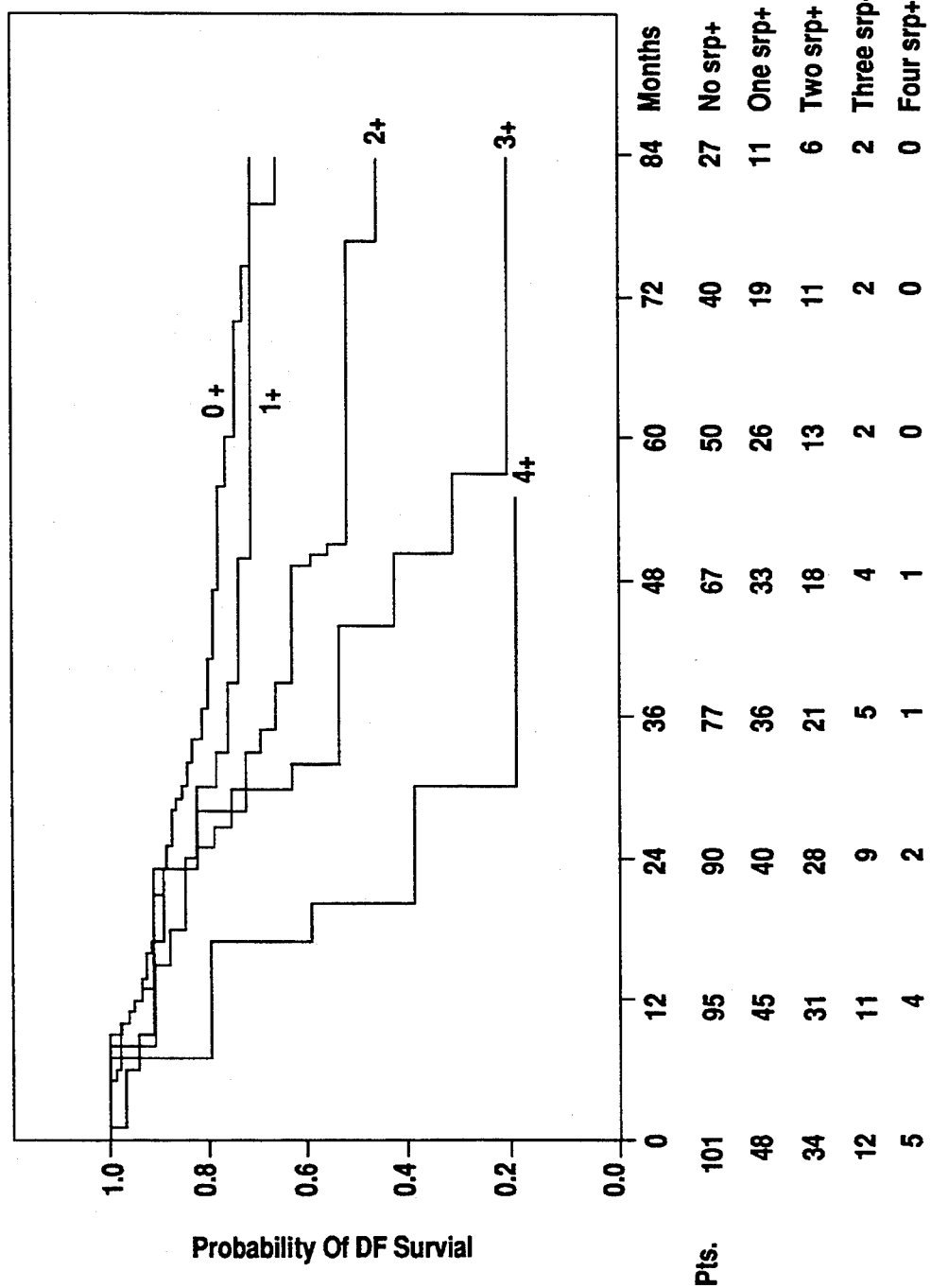
FIG. 4 illustrates Kaplan-Meier recurrence curves for node-negative breast cancer patients based on higher levels of one or more of the stress response proteins.

Kaplan-Meier recurrence curves were constructed based upon the higher levels of any one of the four, two of the four, three of the four, or all four srp's in the tumor, and compared with those containing only low levels of all four srp's (FIG. 4). Concomitant presence of more than one high srp in the tumor was highly indicative of early recurrence of disease. The five-year actuarial recurrence was 24% to 27% in patients with low levels of all four srp's or with high level of only one of the four srp's, 47% in patients with high levels of two of four srp's, and 8% to 80% in patients with high levels of three or all four srp's. Data are shown in Table 4.

TABLE 4

Five-Year Actuarial Recurrence of Node-Negative Breast Cancer Patients as a Function of Stress Response Proteins (srp'a)

| No. of Positive srp's | No. of Patients | % Recurrence ± S.E. |
| --- | --- | --- |
| None | 101 | 24 ± 4 |
| One of four | 48 | 27 ± 7 |
| Two of four | 34 | 47 ± 9 |
| Three of four | 12 | 78 ± 13 |
| All four | 5 | 80 ± 18 |

High levels of srp's, defined in Table 3A, are denoted as positive.

Stress response proteins and several other tumor characteristics were subjected to a multivariate analysis to explore their independent contribution in predicting disease-free survival probability in node-negative breast cancer patients. Ploidy, nuclear grade, and histologic grade were not included in this analysis since values for these variables were not available for many of the tumors.

A partially non-parametric regression model was used to evaluate the predictive power of various combinations and interactions of prognostic factors in a multivariate manner (N. E. Breslow, Int. Stat. Rev. 43, 45 (1975); D. R. Cox, J.R. Stat. Soc. B. 34, 187 (1972); J. D. Kalbfleisch and R. L. Prentice, The Statistical Analysis of Failure Time Data, New York, Wiley, 1980)). Variables were entered stepwise and the relative risks are presented only for the retained variables. Median clinical followup time for patients still living was 74 months with a range of 29 to 154 months.

Stress response (P=0.001) and cathepsin D (P=0.004) appeared as independent predictors of early recurrence, as indicated in Table 5. Relative risk for stress response was 1.4 per additional high srp. Inclusion of ploidy in multivariate analysis did not affect the dominance of srp's and cathepsin D. However, when patients with zero or one high srp were grouped and compared with all patients with two or more high srp's, the statistical significance of srp's was slightly weakened.

TABLE 5

Stress Response Proteins and Other Tumor Characteristics in Multivariate Disease-Free Survival in 199 Node-Negative Breast Cancer Patients

| | | Relative |
| --- | --- | --- |
| Factor | Multivariate P-Value | Risk |
| Stress Response Proteins | 0.001 | 1.4* |
| Cathepsin D | 0.004 | 2.1 |
| Patient Age | 0.08 | |
| Progesterone Receptor | 0.11 | |
| HER-2/neu Protein | 0.13 | |
| Estrogen Receptor | 0.61 | |
| Tumor Size | 0.91 | |

*srp's were considered as an ordinal variable (0 to 4+) so the relative risk is shown as per positive (i.e. high level) srp.

The four srp's analyzed are frequently present in primary breast tumors and are found to be associated with clinical variables suggesting lymph node invasion, tumor aggressiveness, hormone-responsiveness, and histopathologic de-differentiation. Breast cancer patients whose tumors contained lower levels of srp's had a significantly greater likelihood of surviving free of recurrence (second tumor) than patients with higher levels of srp's. Simultaneous occurrence of high levels of more than one srp is a stronger indicator of early disease-recurrence. In multivariate analysis, stress response joins cathepsin D in predicting early tumor metastasis.

Kits useful in the present invention comprise a carrier having compartments to receive several closed containers, the number depending on the specific reagents required for the method of analysis. All kits would provide a first container means comprising a stress response protein standard which contains known levels of hsp27, 70, 90 and grp 94; a second container means comprising a negative control breast tumor extract, a third container means comprising a positive control breast tumor extract, and a fourth container means comprising four monoclonal antibodies to the four stress response proteins. Methods of stress response protein determination could be based on Western Blot, ELISA, or immunohistochemical analysis.

In a Western Blot procedure, a breast tumor sample is pulverized in liquid nitrogen to obtain a uniform distribution of cells, extracted, and total protein determined. After polyacrylamide gel electrophoresis and incubation with the appropriate antibodies, the sample srp bands are measured by densitometry and reported as a ratio against the srp bands of the included standards. The ratios are related to "cutoff" values as described earlier which indicate tumor recurrence risk.

An immunohistochemical method would be useful in kit form. The tumor sample is sectioned and fixed on an adhesive-coated slide which can be provided with the kit. Six sections are incubated with a normal animal serum, then four of these are treated with four different monoclonal antibodies to the stress response proteins and two with antibody negative controls. The antibodies are also applied to four control slides provided with the kit. All sections are incubated with biotinylated second antibody, incubated with avidin and biotinylated peroxidase, then incubated with diaminobenzidine and osmium tetroxide, and stained with methyl green. Positive staining shows brown coloration in the cytoplasm and is quantitated by determining both the fraction of stained tumor cells in several fields and the degree of their positivity to develop an H-score, as is presently done for a number of other proteins.

An ELISA assay kit would provide the monoclonal antibodies to the stress response proteins, the stress response protein standards, positive and negative breast tumor cytosol controls, and a second set of monoclonal antibodies to the stress response proteins coupled to horseradish peroxidase.

EXAMPLE 1

Detection and Measurement of Stress Response Proteins

Total proteins from tumor tissues or cell pellets were extracted with sodium dodecyl sulfate (SDS). Protein concentration in the SDS-extract was determined by the BCA method (P. K. Smith et al., *Anal. Biochem.* 150, 76 (1985)). SDS-extracted proteins were mixed with a sample buffer to achieve a final concentration of 135 mM Tris (pH 6.8), 2% SDS, 10% glycerol, 5% dithiothreitol, and 0.01% pyronin dye and the samples were heated in a boiling water bath for five minutes.

Tumor proteins (100 μg) were resolved on 10% polyacrylamide vertical slab gels using 3% stacking gel. An SDS extract of MCF-human breast cancer cells was included at three concentrations (100 μg, 50 μg, and 25 μg protein, corresponding to 100, 50 and 25 arbitrary units of each stress response protein) in each gel as an internal reference standard.

Transfer of separated proteins onto 0.2μ nitroscreens (DuPont) was performed at 200 mAmp for 16 hours at 4° C. Following blocking of non-specific sites with 5% condensed milk powder (Carnation) for 1 hour, blots were incubated with culture supernatant of a hybridoma clone secreting rat monoclonal antibody (MAb) to grp94 (clone 9G10) overnight at 4° C. $^{125}$I-labeled sheep anti-rat IgG (100,000 cpm/ml; Amersham Corp) was used as the second antibody. After washing, the blots were exposed for 20-24 hours to X-OMAT X-ray film (Kodak) at −70° C. The same membranes were next reacted with purified mouse MAb to hsp70 (C92) at 1 μg/ml followed by $^{125}$I-labeled sheep anti-mouse IgG (100,000 cpm/ml; Amersham Corp) and exposed to X-ray film as described above, and then incubated with a mouse MAb to hsp27 (1 μg/ml) again followed by radiolabeled second antibody and x-ray film autoradiography.

For measuring hsp90, another set of gels was run under the same conditions as described above and membranes were incubated with a mouse MAb (AC88, 1 μg/ml) followed by incubation with $^{125}$I-labeled anti-mouse IgG second antibody and exposure to X-ray film. The level of srp's in individual tumors was quantitated by densitometric scanning of the pertinent band on the autoradiogram in a Beckman DU-7 spectrophotometer, and expressed in relative units by comparison with the MCF-7 internal reference standard.

The srp values in FIG. 1 for ten tumors (1 to 10) were: 33, 85, 19, 46, 70, 74, 54, 54, 27, 108 for grp94; 23, 76, 13, 50, 32, 58, 6, 16, 4, 12 for hsp90; 63, 261, 75, 119, 46, 211, 46, 211, 86, 86 for hsp70; and 194, 245, 41, 179, 91, 112, 5, 61, 139, 31 for hsp27.

EXAMPLE 2

Determination of Optimum Cutoff Values

Cutoff values for the four srp's that best distinguish patients at high risk for relapse were established by determining P-values for disease-free survival using each possible cutoff value. FIG. 2 graphically displays these P-values for both node-positive and node-negative breast cancer patients. A horizontal line is drawn at the P=0.05 level to show statistical significance. Upward arrows indicate the optimum cutpoints. Range and optimum cutoff values for the four srp's in node-negative breast cancer patients are given below:

| # Cutpoint | Range and Optimum Cutoff Values for srp's in Breast Tumors | | |
|---|---|---|---|
| | Stress Response | Cutoff Range | Optimum |
| 1. | grp94 | 45 units | 45 units |
| 2. | hsp90 | 12–59 units | 32 units |
| 3. | hsp70 | 120–250 units | 217 units |
| 4. | hsp27 | 46–232 units | 126 units |

EXAMPLE 3

Determination of Recurrence Relative to Stress Response Protein Level

Based on optimum cutoff determinations, high srp's are defined as follows: grp94≧45 units, hsp90≧32 units, hsp70≧217 units, and hsp27≧126 units per 100 μg tumor proteins. Patients were followed for disease-free survival. Any post-surgical appearance of malignancy either near to or distant from the operated breast was considered as recurrence of disease. Survival curves were constructed and shown in FIG. 3 (E. L. Kaplan and P. Meier, *J. Am. Stat. Assoc.* 53, 457 (1958)) and the log rank test for censored survival data was used to test the statistical significance of difference between the curves (N. Mantel, *Cancer Chemother. Rep.* 50, 163 (1966)). All computations were done with the Biomedical Computer Programs-P series. The recurrence curves were based on a clinical followup period of 29 to 154 months, with a median of 74 months for patients still alive at the time of analysis. Values below the X-axis indicate the number of patients at risk at the interval shown.

EXAMPLE 4

Determination of Disease-Free survival Relative to Number of High Level Stress Response Proteins Survival curves as a function of the number of srp's found to exceed their cutoff values are shown in FIG. 4. Positive (high) levels are the same as described in Example 3. Median followup was 74 months. Values below the X-axis show the number of patients at risk at the indicated time interval. Statistical significance (P-value) for pairwise comparisons between groups of patients separated according to the number of their high level srp's is given below.

| | No srp+ | One srp+ | Two srp+ | Three srp+ | Four srp+ |
|---|---|---|---|---|---|
| No srp+ | | | | | |
| One srp+ | 0.6 | | | | |
| Two srp+ | 0.01 | 0.1 | | | |
| Three srp+ | 0.0006 | 0.009 | 0.2 | | |
| Four srp+ | 0.0001 | 0.002 | 0.04 | 0.2 | |

EXAMPLE 5

Standard for the Measurement of Stress Response Proteins

MCF-7 human breast cancer cells (originally obtained from the Michigan Cancer Foundation), ATCC HTB22 MCF-7 were cultured in Eagle's minimum essential medium (MEM) supplemented with 10 mM HEPES, 1% non-essential amino acids (Gibco), 2 mM L-glutamine (Gibco), 25 $\mu$g/ml gentamycin (Irvine Scientific), 6 ng/ml bovine insulin, and 5% calf serum (K.C. Biologicals). Sodium bicarbonate (0.2%) was added to adjust the final pH to approximately 7.2. Cells were allowed to grow at 37° C. in an atmosphere containing 5% $CO_2$. Logarithmically growing MCF-7 cells close to confluency (75–100%) were harvested by a brief incubation with 1 mM EDTA in phosphate buffered saline (PBS). Cells were washed twice with PBS, and pelleted. Cell pellets were exposed to 5% sodium dodecyl sulfate (SDS), vortexed, and kept in a boiling water bath for 5 minutes, revortexed, and allowed to cool to room temperature for about 15 minutes. Clear supernatant was collected after spinning the tubes in a centrifuge. Protein concentration in the SDS extracts was determined by the BCA method (P. K. Smith et al., *Anal. Biochem.* 150, 76 (1985)). For the estimation of quantity of stress response proteins (srp's) in breast tumors by Western Blot, this SDS extract of MCF-7 human breast cancer cells was included in each gel at three concentrations (100 $\mu$g, 50 $\mu$g, and 25 $\mu$g protein, corresponding to 100, 50, and 25 units). The level of srp's in breast tumors was expressed in units relative to this standard.

The following examples, 6, 7, and 8, illustrate how stress response proteins could be analyzed by convenient kit means. The examples have not been tested using precisely the steps outlined but are illustrative of how such kits would be used.

EXAMPLE 6

This Example Illustrates the Steps that Could be Used in a Western Blot Kit for Stress Response Protein Determination Mechanically pulverize the breast tumor specimen in liquid nitrogen to obtain a uniform distribution of tumor cells. Add 1 ml of 5% sodium dodecyl sulfate to 100 mg of tumor powder and vortex. Place the tube in a boiling water bath for 5 min and vortex. Centrifuge the tube at 13,000$\times$g for 2 min and determine protein concentration in the clear supernatant using BCA reagents by mixing reagent A and B in a 50:1 ratio. Add 1 ml of this mixture to a 100 $\mu$l aliquot of test diluted sample or protein standard.

Incubate at room temperature for 1 hour, read absorbance at 562 nm, and calculate protein concentration by interpolation on the protein standard curve constructed based on the protein standard used in each experiment. Electrophorese 100 $\mu$g of solubilized tumor proteins on 10% polyacrylamide Laemmli gel under denaturing, reducing conditions. On each gel load the stress response proteins standard (vial 1) and tumor extracts from vial 2A and 2B as positive and negative controls. Electrically transfer proteins from the gel to nitroscreen filter (Towbin's procedure) using 200 mAmp current for 16 hours in the cold. Block nitroscreen by incubation for 1 hour at room temperature with 5% evaporated milk in PBS. Incubate nitroscreen with 1:50 fold dilution (prepared in 5% milk) of antibodies to stress-response proteins (vial 3) for 2 hours at room temperature with gentle shaking. Wash nitroscreen 3 times for 5 minutes each with phosphate buffered saline (PBS) on a shaker at room temperature. Incubate nitroscreen with 1:500 fold dilution (in 5% milk) of radioactive second antibody (vial 4) for 1 hour at room temperature with gentle shaking. Wash nitroscreen 3 times for 5 minutes each with PBS on a shaker at room temperature. Expose nitroscreen overnight to x-ray film at −70° C. Develop film and estimate the amount of four srp's in tumor specimen by densitometry of the relevant bands and calculation of ratios with the srp standard bands. High levels of srp's are defined as follows: grp94$\geq$45 units, hsp90$\geq$32 units; hsp70$\geq$217 units, and hsp27$\geq$126 units per 100 $\mu$g of tumor proteins.

EXAMPLE 7

This Example Illustrates the Steps that Could be Used in the Immunohistochemical Determination of Stress Response Proteins by a Kit Method Cut six 5-micron sections from the frozen OCT block of a breast tumor specimen and place each section on a separate adhesive-coated microscope slide provided with the kit. Air dry tissue sections for 30 minutes at room temperature (RT). Dip slides in −20° C. acetone for 5 minutes. (For formalin-fixed paraffin-embedded tumors, cut six 5-micron sections from the paraffin block. Bake at 60° C. for 30 minutes in an oven. Dip slides in xylene 2-times for 5 minutes each. Place slides 2-times in 100% alcohol for 5 minutes each. The rest of the procedure is common to both frozen and fixed tumors. Wash 2-times with PBS for 2 minutes each. Place slides for 30 minutes in PBS containing 0.1% $H_2O_2$ and 0.1% sodium azide. Wash 2-times with PBS for 2 minutes each. Cover tissue sections with 10% normal goat serum (vial 1) for 30 minutes at RT. Drain the solution and incubate four sections of the test tumor with four different monoclonal antibodies to srp's (vial 2A, 2B, 2C, 2D) at the dilution indicated on each vial.

Similarly apply these antibodies to four control slides provided with the kit (control slides of breast tumor sections showing positive staining for srp's). Treat two remaining sections of the test tumor with the antibody negative controls (3A, 3B). Incubate all ten slides in a covered humidity chamber for 3 hours at RT. Wash 2-times with PBS for 2 minutes each. Incubate sections for 30 minutes at RT with appropriate biotinylated second antibody (4A or 4B) at the indicated dilution (sections treated with grp94 antibody or normal rat antibody control are treated with anti-rat second antibody (4A), while all other sections are treated with anti-mouse second antibody (4B)). Wash 2-times with PBS for 2 minutes each.

Mix reagents from vial 5A and 5B as indicated on the vials to prepare avidin-biotin-peroxidase complex and apply to the sections for 30 minutes at RT. Wash 2-times with PBS for 2 minutes each. Incubate sections with diaminobenzidine (vial 6) dissolved as instructed in PBS containing 0.03% $H_2O_2$. Wash 2-times with PBS for 2 minutes each. Place slides in osmium tetroxide solution (vial 7) for 30 seconds. Wash with deionized water for 2 minutes and place in 0.5% methyl green for 2 minutes. Wash with deionized water for 2 minutes and dehydrate tissue by dipping in increasing concentrations of alcohol and finally in xylene. Cover with permount, place cover slip on the tissue and dry. View tissue sections under a microscope. Positive staining shows brown coloration in the cytoplasm.

EXAMPLE 8

This Example is Illustrative of Steps that Would be Utilized in an ELISA Kit Determination of Stress Response Proteins Coat 96-well microtiter places with a monoclonal antibody to srp (monoclonal antibodies to four different srp's are provided with the kit; vial 1A-1D). Incubate plates overnight at 4° C. with the antibody solution (100 μl/well) at 5 μg/ml in sodium carbonate buffer pH 9.6, or alternatively antibody-coated microtiter plates can be provided with a kit. Wash plates with PBS 3-times and incubate with 1% BSA in PBS for 1 hour at room temperature (RT). Wash with PBS 6-times. Dispense 100 μl/well test breast tumor cytosols, positive and negative controls (vial 2A, 2B) and standards (vial 3A-3D). Incubate at RT for 2 hours with gentle agitation. Wash with PBS 6-times. Incubate with 100 μl/well of a second set of anti-srp monoclonal antibodies labelled with horseradish peroxidase (vial 4A-4D) for 1 hour at RT. Wash with PBS 6-times. Add 100 μl/well of orthophenylene diamine (OPD) solution. Incubate in the dark at RT for 15 minutes. Stop reaction by adding 100 μl/well sulfuric acid and record absorbance at 490 nm.

Construct standard curve by plotting absorbance against srp concentration. Calculate srp concentration in test cytosols by interpolation of their absorbance on the standard curve.

EXAMPLE 9

This Example Illustrates the Procedure Contemplated by the Applicants as useful in Determining the Level of Stress Response Protein by Measuring mRNA Levels The example is illustrated with hsp90, but would be appropriate for other hsps, including hsp27, hsp70 and grp94. Amino acid sequences for these hsps are known, thus DNA sequences are readily determined and cDNA obtained by well-known cloning procedures. Details of the general steps may vary but generally procedures for determining mRNA levels are routinely used by those of skill in the art.

Determination of HSP90 Levels in Tumor Tissue

Pulverized tumor tissue samples are homogenized in guanidine isothiocyanate and total cellular RNA extracted by standard extraction techniques for RNA. After precipitation with ethanol, RNA pellets are resuspended in water and checked for absorbance at 320 nm. The procedure is repeated as necessary to obtain preparations free of protein contamination, as indicated by lack of absorbance at 320 nm. RNA concentrations are adjusted to 1 μg/ml. Northern blot hybridization is performed using labeled riboprobes. The probes for hsp90 are prepared as described (Hickey, L., Brandon, L. E., Smale, G., LLoyd, D. and Weber, L. A., *Mol. Cell* 9, 2615–2625 (1989) from single-stranded probes obtained from fragments cloned in M13 using standard hybridization procedures. Probes are labelled with [$^{35}$S]UTP. Hybridization is quantitated by densitometry.

The references cited within the text are incorporated herein by reference to the extent that they supplement, explain, provide a background for or teach methodology, techniques and/or compositions employed herein.

We claim:

1. An in vitro method for prognosis of disease-free survival of individuals having a breast cancer tumor, comprising determining if at least two selected stress response proteins are overproduced in a sample of such a tumor, such an overproduction correlating negatively with disease-free survival.

2. The method of claim 1 wherein overproduction is determined by measuring the levels of mRNAs which encode the selected stress response proteins.

3. The method of claim 1 wherein overproduction is determined by measuring protein levels for selected stress response proteins.

4. The method of claim 1 wherein overproduction is determined by determining the number of stress response proteins that are detectable in breast tumor tissue or in blood, serum or plasma samples.

5. The method of claim 1, further defined as
   determining the level of production of said selected stress response proteins; and
   determining if said level of production comprises an overproduction that is above a basal level.

6. The method of claim 5 wherein basal levels of the selected stress response proteins are determined relative to levels of said proteins produced by cultured cells that are capable of producing stress response proteins in vitro.

7. The method of claim 6 wherein the cultured cells are cancer cells, normal cells, genetically engineered cells or progeny of said cells.

8. An in vitro method for predicting the risk of tumor recurrence in individuals having a selected tumor, comprising determining if at least two selected stress response proteins are overproduced in a sample of such a tumor, such an overproduction correlating positively with a likelihood of tumor recurrence.

9. The method of claim 8, further defined as comprising:
   determining an overproduction level for selected stress response proteins, said level being in excess of a minimum amount statistically determined to related tumor recurrence;
   determining the levels of the selected stress response proteins in tumor sample; and
   predicting a risk of tumor recurrence wherein an overproduction level of at least two stress response proteins in the tumor sample is positively associated with the likelihood of tumor recurrence.

10. The method recited in claim 1, 5 or 8 wherein the stress response proteins have molecular weight of 94 kDa, 80 to 90 kDa, 68 to 74 kDa, or 18 to 30 kDa.

11. The method of claim 1, 5, or 8 wherein at least two of the following stress response proteins are assessed: hsp27, hsp70, hsp90 and grp94.

12. The method of claim 1 wherein the breast tumor is in a node negative breast cancer patient.

13. The method of claim 11 wherein determining the stress response proteins comprises comparing levels of the stress response proteins in said samples with levels of said stress response proteins from breast cell cancer line MCF-7, wherein a negative correlation with disease free probability exists when at least two of the following are determined:
   sample grp94 is at least 45% of grp94 in cancer cell line standard MCF-7 from an amount of protein in said standard equivalent to that of the tissue sample;
   sample hsp27 is at least 46% of hsp27 in cancer cell line standard MCF-7 from an amount of protein in said standard equivalent to that of the tissue sample;

sample hsp90 is at least 12% of hsp90 in cancer cell line standard MCF-7 from an amount of protein in said standard equivalent to that of the tissue sample; or sample hsp70 is at least 120% of hsp70 in cancer cell line standard MCF-7 from an amount of protein in said standard equivalent to that of the tissue sample.

14. The method of claim 11 wherein an optimal cutoff overproduction level obtained relative to standard breast cell line MCF-7 comprises:
   (a) 126 units per 100 μg tumor proteins for hsp27;
   (b) 217 units per 100 μg tumor proteins for hsp70;
   (c) 32 units per 100 μg tumor proteins for hsp90; or
   (d) 45 units per 100 μg tumor proteins for grp94.

15. A kit for the immunologic assessment of breast tumor recurrence or survival, the kit comprising:
   (a) at least one aliquoted antibody which specifically binds a stress response protein selected from the group consisting of hsp90, hsp27, and grp94 provided that antibodies which specifically bind hsp27 are included with at least one other of said antibodies; and
   (b) an immunologic detection reagent.

16. The kit of claim 15, wherein the immunologic detection reagent comprises a radioisotopic, fluorometric, enzymatic or colorimetric label.

17. The kit of claim 16, wherein said label is associated with a secondary antibody.

18. The kit of claim 15, specifically adapted for Western Blot detection and measurement of tumor-associated stress response proteins, the kit comprising:
   a carrier being compartmentalized to receive one or more container means in close confinement therein;
   a first container means comprising a stress response protein standard;
   a second container means comprising a negative control;
   a third container means comprising a positive control;
   a fourth container means comprising one or more separate compartments each comprising a first antibody which specifically binds a stress response protein selected from the group consisting of hsp70, hsp90, hsp27 grp94 provided that antibodies which specifically bind hsp27 are included with at least one other of said antibodies; and
   a fifth container means comprising one or more separate compartments each comprising labeled second antibodies which specifically bind the first antibodies.

19. The kit of claim 18 wherein the stress response protein standard, the positive and negative controls, and the antibodies are in lyophilized or liquid form.

20. The kit of claim 15, specifically adapted for use in the immunohistochemical determination of stress response proteins in tumor tissue comprising:
   a carrier being compartmentalized to receive one or more container means in close confinement therein;
   a first container means comprising a normal serum from a first animal;
   a second container means comprising separate vials each comprising antibodies derived from a second or third animal, each antibody being directed to a different stress response proteins;
   a third container means comprising two separate vials, the first vial comprising a biotinylated antibody from a fourth animal specifically binding antibodies from the second animal, the second vial comprising a biotinylated antibody from a first, fourth, or fifth animal specifically binding antibodies from the third animal;
   a fourth container means comprising an antibody negative control obtained from the second animal;
   a fifth container means comprising an antibody negative control obtained from the third animal; and
   a sixth container means comprising control slides with tumor sections.

21. The kit of claim 20 wherein the biotinylated antibody from a fourth animal can also be from the first animal.

22. The kit of claim 21 wherein the biotinylated second antibodies comprising the third container are anti-rat and anti-mouse biotinylated antibodies.

23. The kit of claim 20 wherein the antibody negative controls comprising the fourth and fifth container are normal rat and normal mouse IgG.

24. An in vitro method for prognosis of disease free survival in breast cancer patients having or once having a tumor, comprising determining if at least two selected stress response proteins or related metabolites are overproduced in a sample of such tumor or in a blood, serum., or plasma sample, such an overproduction correlating negatively with disease-free survival.

* * * * *

UNITED STATES PATENT AND TRADEMARK OFFICE
CERTIFICATE OF CORRECTION

PATENT NO. : 5,447,843

DATED : September 5, 1995

INVENTOR(S) : William L. McGuire, Gary M. Clark, Gary C. Chamness, Atul K. Tandon and Suzanne A. Fuqua It is certified that error appears in the above-identified patent and that said Letters Patent is hereby corrected as shown below:

In claim 10, column 24, line 48, delete "weight" and insert "weights".

Signed and Sealed this

Seventh Day of November, 1995

BRUCE LEHMAN

Attest:

Attesting Officer

Commissioner of Patents and Trademarks